(12) United States Patent
Landesberg et al.

(10) Patent No.: US 11,547,307 B2
(45) Date of Patent: Jan. 10, 2023

(54) QUANTIFICATION OF THE RESPIRATORY EFFORT FROM HEMODYNAMIC MEASUREMENTS

(71) Applicant: TECHNION RESEARCH AND DEVELOPMENT FOUNDATION LTD., Haifa (IL)

(72) Inventors: Amir Landesberg, Haifa (IL); Anna Faingersh-Klebanov, Haifa (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 351 days.

(21) Appl. No.: 16/887,246

(22) Filed: May 29, 2020

(65) Prior Publication Data
US 2021/0068667 A1    Mar. 11, 2021

Related U.S. Application Data

(60) Provisional application No. 62/839,848, filed on Apr. 29, 2019.

(51) Int. Cl.
*A61B 5/0205* (2006.01)
*A61B 5/021* (2006.01)
*A61B 5/08* (2006.01)
*A61B 5/00* (2006.01)

(52) U.S. Cl.
CPC ........ *A61B 5/0205* (2013.01); *A61B 5/02108* (2013.01); *A61B 5/0816* (2013.01); *A61B 5/746* (2013.01)

(58) Field of Classification Search
CPC .................................................. A61B 5/0205
See application file for complete search history.

(56) References Cited

U.S. PATENT DOCUMENTS

| | | | | |
|---|---|---|---|---|
| 2005/0085865 A1* | 4/2005 | Tehrani | ............. | A61N 1/36132 607/42 |
| 2008/0243016 A1* | 10/2008 | Liao | ..................... | A61B 5/0205 600/300 |
| 2010/0076514 A1* | 3/2010 | Cho | ..................... | A61B 5/0205 607/18 |

(Continued)

OTHER PUBLICATIONS

Yancy CW, Jessup M, Bozkurt B, et al. "2013 ACCF/AHA Guideline for the Management of Heart Failure",. Journal of the American College of Cardiology. 2013 vol. 62, No. 16, pp. e147-e239 (2013).

(Continued)

*Primary Examiner* — Travis R Hunnings
(74) *Attorney, Agent, or Firm* — Browdy and Neimark, PLLC

(57) ABSTRACT

A method for detecting or monitoring respiratory or cardiac health of a patient includes measuring any intravascular or intracardiac pressure (IVP) of a patient over a period of time, said IVP including a measured respiratory wave, defining respiratory effort of the patient as a peak-to-peak amplitude of said respiratory wave, and using the respiratory effort to detect or monitor respiratory and cardiac health of the patient by comparing the respiratory effort with a known value of respiratory effort or by monitoring changes in the respiratory effort of the patient over another period of time.

24 Claims, 4 Drawing Sheets

(56) References Cited

U.S. PATENT DOCUMENTS

| | | | | |
|---|---|---|---|---|
| 2012/0029361 | A1* | 2/2012 | Addison | A61B 5/02125 600/484 |
| 2012/0041279 | A1* | 2/2012 | Freeman | A61B 5/0816 600/534 |
| 2012/0310050 | A1* | 12/2012 | Osorio | G16H 20/40 600/300 |

OTHER PUBLICATIONS

Parshall MB, Welsh JD, Brockopp DY, Heiser RM, Schooler MP, Cassidy KB, "Dyspnea duration, distress, and intensity in emergency department visits for heart failure", Heart & Lung: The Journal of Acute and Critical Care, ;vol. 30, No. 1, pp. 47-56 (2001).

Patel H, Shafazand M, Schaufelberger M, Ekman I., "Reasons for seeking acute care in chronic heart failure", European Journal of Heart Failure, vol. 9, No. 6-7, pp. 702-708 (2007).

Klein L., "Treating Hemodynamic Congestion Is the Key to Prevent Heart Failure Hospitalizations", JACC: Heart Failure, vol. 4, No. 5, pp. 345-347 (2016).

Shochat MK, Shotan A, Blondheim DS, et al., "Non-invasive Lung Impedance-Guided Preemptive Treatment in Chronic Heart Failure Patients: A Randomized Controlled Trial (Impedance-HF Trial).", Journal of Cardiac Failure. Vol. 22, No. 9, pp. 713-722 (2016).

Meyer F J, Zugck C, Haass M, et al., "Inefficient ventilation and reduced respiratory muscle capacity in congestive heart failure", Basic Res Cardiol., vol. 95 No. 4, pp. 333-342 (2000).

Zile Wir, Bennett TD, St. John Sutton M, et al., "Transition From Chronic Compensated to Acute Decompensated Heart Failure: Pathophysiological Insights Obtained From Continuous Monitoring of Intracardiac Pressures", Circulation, vol. 18(No. 14)pp. 1433-1441 (2008).

Galie N, Humbert M, Vachiery J-L, et al., "2015 ESC/ERS Guidelines for the diagnosis and treatment of pulmonary hypertension", European Heart Journal, vol. 37(No. 1), pp. 67-119 (2016).

Guazzi Marco, Borlaug Barry A., "Pulmonary Hypertension Due to Left Heart Disease", Circulation, vol. 26(No. 8), pp. 975-990 (2012).

Abraham WT, Adamson PB, Bourge RC, et al., "Wireless pulmonary artery haemodynamic monitoring in chronic heart failure: a randomised controlled trial", The Lancet, vol. 377(No. 9766), pp. 658-666 (2011).

Abraham WT, Stevenson LW, Bourge RC, Lindenfeld JA, Bauman JG, Adamson PB, Sustained efficacy of pulmonary artery pressure to guide adjustment of chronic heart failure therapy: complete follow-up results from the CHANIPION randomised trial:, Lancet, vol. 387(No. 10017) pp. 453-461 (2016).

Cherniack RM, Cuddy TE, Armstrong JB., "Significance of Pulmonary Elastic and Viscous Resistance in Orthopnea", Circulation, vol. 5(No. 6), pp. 859-864 (1957).

Guntheroth WG, Luchtel DL, Kawabori I, "Pulmonary microcirculation: tubules rather than sheet and post" Journal of Applied Physiology, vol. 53(No. 2), pp. 510-515 (1982).

Schittny JC, Mund SI, Stampanoni M., Evidence and structural mechanism for late lung alveolarization, American Journal of Physiology—Lung Cellular and Molecular Physiology, vol. 294No. (2), pp. L246-L254 (2008).

Hughes R, May AJ, Widdicombe JG, "The effect of pulmonary congestion and oedema on lung compliance", The Journal of physiology, vol. 42(No. 2) pp. 306-313 (1958).

Hauge A, Bo G, Waaler BA., "Interrelations between pulmonary liquid volumes and lung compliance", Journal of Applied Physiology, vol. 98(No. 4) pp. 608-614 (1975).

Petak F, Habre W, Hantos Z, Sly PD, Morel DR, "Effects of pulmonary vascular pressures and flow on airway and parenchymal mechanics in isolated rat lungs", Journal of Applied Physiology, vol. 92(No. 1), pp. 169-178 (2002).

Lalande S, Luoma CE, Miller AD, Johnson BD,"Effect of changes in intrathoracic pressure on cardiac function at rest and during moderate exercise in health and heart failure", Experimental Physiology, vol. 97(No. 2) pp. 248-256 (2011).

Pinsky MR, "Cardiopulmonary Interactions: Physiologic Basis and Clinical Applications", Annals of the American Thoracic Society, vol. 15(Supplement I), pp. S45-S48 (2017).

Karam M, Wise RA, Natarajan TK, Permutt S, Wagner HN, "Mechanism of decreased left ventricular stroke volume during inspiration in man, "Circulation vol. 69(No. 5) pp. 866-873 (1984).

Peters J, Kindred MK, Robotham JL,"Transient analysis of cardiopulmonary interactions. II. Systolic events", Journal of Applied Physiology, vol. 64(No. 4), pp. 1518-1526 (1988).

Naughton Matthew T., Rahman M. Atiar, Hara Kazuhiro, Floras John S., Bradley T Douglas, "Effect of Continuous Positive Airway Pressure on Intrathoracic and Left Ventricular Transmural Pressures in Patients With Congestive Heart Failure", Circulation, vol. 95;91(No. 6), pp. 1725-1731 (1995).

Yu C-M, Wang L, Chau E, et al., "Intrathoracic impedance monitoring in patients with heart failure: correlation with fluid status and feasibility of early warning preceding hospitalization", Circulation vol. 112(No. 6), pp. 841-848 (2005).

Harik-Khan RI, Wise RA, Fozard JL., "Determinants of Maximal Inspiratory Pressure", Am J Respir Crit Care Med. vol. 158(No. 5) pp. 1459-1464 (1998).

Walsh JT, Andrews R, Johnson P, Phillips L, Cowley AJ, Kinnear WJ, "Inspiratory muscle endurance in patients with chronic heart failure", Heart, vol. 76(No. 4), pp. 332-336 (1998).

Dall'Ago P, Chiappa GRS, Guths H, Stein R, Ribeiro JP,"Inspiratory Muscle Training in Patients With Heart Failure and Inspiratory Muscle Weakness: A Randomized Trial", Journal of the American College of Cardiology, vol. 47(No. 4), pp. 757-763 (2006).

Waisman D, Faingersh A, Levy C, et al.,"Transient decrease in PaCO 2 and asymmetric chest wall dynamics in early progressing pneumothorax", vol. 39, pp. 137-145 (2012).

Evans SA, Watson L, Cowley AJ, Johnston DA, Kinnear WM, Kinnear WJM, "Static lung compliance in chronic heart failure: relation with dyspnoea and exercise capacity", Thorax, pp. 245-248 (1995).

Lang SA, Duncan PG Shephard DAE, Ha CH", Pulmonary oedema associated with airway obstruction", Can Janaesth, vol. 37(No. 2), pp. 210-218 (1990).

West JB, Mathieu-Costello O. "Stress failure of pulmonary capillaries: role in lung and heart disease" The Lancet. vol. ;340(8822), pp. 762-767 (1992).

West JB, Mathieu-Costello O. "Vulnerability of Pulmonary Capillaries in Heart Disease" Circulation, vol ;92(No. 3) pp. 622-631 (1995).

Moran G, Folch H. "Exercise-induced pulmonary haemorrhage in horses—review," Acta Vet Brno. vol. ;82(No. 3) pp. 309-316 (2013).

Search Report dated Aug. 3, 2021, for corresponding application PCT/MX 20/00016.

Written Opinion dated Aug. 3, 2021, for corresponding application PCT/MX 20/00016.

\* cited by examiner

QUANTIFICATION OF THE RESPIRATORY EFFORT FROM HEMODYNAMIC MEASUREMENTS

FIELD OF THE INVENTION

The present invention generally relates to methods for quantification of the respiratory effort from hemodynamic measurements.

BACKGROUND OF THE INVENTION

Dyspnea is a cardinal manifestation of heart failure (HF) and a primary reason for HF patients, rehospitalization and emergency department visits. Clinical symptoms and signs of cardiac decompensation, as dyspnea and rales, are related to the development of lung (clinical) congestion. The clinical congestion is preceded by a latent gradual development of hemodynamic congestion. The duration of the hemodynamic congestion, from the development of substantial elevation in the left atrial pressure (LAP) to the occurrence of clinical congestion with HF related events as hospitalization, is few days to several weeks. A gradual increase in the end-diastolic pulmonary artery pressure (ePAD), a surrogate of the LAP, may be a sign for the development of cardiac decompensation. An increase in the LAP leads to a retrograde rise in the pulmonary venous pressure, pulmonary capillary wedge pressure (PCWP) and to the development of pulmonary hypertension (PH). A prior art study investigated the utility of monitoring the pulmonary artery pressure (PAP) in management of HF patients by implanting a miniature device in the pulmonary artery. The study suggested that monitoring the PAP can provide early detection of deteriorating hemodynamic congestion, and can reduce the rate of rehospitalization for cardiac decompensation by 33%. These findings have indicated that a progressive increase in the PAP is an early subclinical hallmark for insidious decompensation that would require inpatient care.

The hemodynamic and clinical congestions increase the respiratory effort required to maintain the ventilation. Fluid congestion turns the lung from an apparent pure elastic tissue into a viscoelastic tissue, leading to an increase in the resistance to air flow. The viscous resistance yields wide hysteresis in the pressure-flow loops, leading to a significant increase in the respiratory effort. Lung congestion is also associated with restrictive ventilatory pattern, considerably before the development of pulmonary edema or pleural effusion. The restrictive decrease in the inspiratory volume capacity is attributed to interstitial edema and congestion of the blood vessels, which further increases the respiratory effort.

The subclinical hemodynamic congestion has detrimental effect on lung compliance. The lung compliance is mainly determined by the alveolar compartment of the respiratory system. Each alveolus is surrounded by a dense capillary network that eventually forms a continuous sheet of blood around the alveolus. Increased pulmonary capillary pressure increases the stiffness of the alveolar walls and decreases the overall lung compliance. The decrease in lung compliance significantly increases the respiratory effort.

Thus, the gradual increase in the pulmonary circulation pressure (hemodynamic congestion) and the development of fluid congestion (clinical congestion) decrease lung compliance, increase lung viscosity and resistance to airflow. These changes in lung mechanical properties demand a significant increase in the respiratory work to maintain the adequate alveolar ventilation, which may be associated with dyspnea.

SUMMARY OF THE INVENTION

The present invention seeks to provide a method for quantification of the respiratory effort from hemodynamic measurements.

Heart failure (HF) is associated with elevated pulmonary capillary wedge pressure (PCWP) and hemodynamic congestion before the development of clinical congestion. The invention aims to detect subclinical increase in the respiratory effort, even before the patients report they suffer from dyspnea.

The current practice is to measure the pressures in the various vascular compartments within the chest and to calculate the mean pressures, systolic and diastolic pressures over a time interval of several breath cycles. Some physicians ask the patient to stop breathing at the end of the expiration phase, and measure the hemodynamic indices without the "noise" introduced by breathing. The inventors have investigated the relationship between the respiratory effort and the hemodynamic indices, the ability to separate between the pure cardiac and respiratory waves, and the ability to quantify the severity of dyspnea.

The inventors have identified tight correlations between the severity of the respiratory effort and the measured pulmonary hemodynamics indices. These effects were explored by simultaneously measuring the hemodynamic indices and the respiratory mechanics in patients undergoing right heart catheterization (n=55) for the diagnosis of dyspnea or pulmonary hypertension.

The PCWP was decomposed into cardiac and respiratory waves. The respiratory effort (PRESP) was defined as the respiratory wave amplitude that modulates the PCWP.

The results of the inventors' study are that HF patients exhibited huge PRESP of 9.0±3.2 mmHg, about 3.5 fold the mean normal PRESP. Their PCWP and PAP rose with PRESP by 1.35±0.40 and 2.70±0.47 mmHg for 1 mmHg of PRESP, respectively. The PCWP also rose with PRESP in patients with lung diseases.

The inventors have discovered tight interactions between the pulmonary circulation and lung mechanics. The measured respiratory effort is a hallmark of HF. An increase in the respiratory effort is associated with an increase in the PWCP, PAP and the pulmonary vascular resistance. Therefore measurement and monitoring of the respiratory effort can assist in evaluation of the severity of HF and in optimization of the treatment.

There is provided in accordance with an embodiment of the invention a method for detecting or monitoring respiratory or cardiac health of a patient, including measuring any intravascular or intracardiac pressure (IVP) within a chest of a patient over a period of time, the IVP including a measured respiratory wave, defining respiratory effort of the patient as a peak-to-peak amplitude of the respiratory wave, and using the respiratory effort to detect or monitor respiratory and cardiac health of the patient by comparing the respiratory effort with a known value of respiratory effort or by monitoring changes in the respiratory effort of the patient over another period of time.

There is provided in accordance with an embodiment of the invention tangible computer-readable device having instructions stored thereon that, when executed by at least one computing device, causes the at least one computing device to perform operations including measuring any IVP within a chest of a patient over a period of time, the IVP including a measured respiratory wave, defining respiratory effort of the patient as a peak-to-peak amplitude of the respiratory wave, and using the respiratory effort to detect or monitor respiratory and cardiac health of the patient by comparing the respiratory effort with a known value of respiratory effort or by monitoring changes in the respiratory effort of the patient over another period of time.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Methods

The study done by the inventors was conducted at the Rambam healthcare campus (Haifa, Israel), and it was approved by the Helsinki ethics committee. All the patients provided written informed consent. The study enrolled patients that underwent diagnostic right heart catheterization (RHC). The standard RHC hemodynamic measurements of the right atrium pressure (RAP), right ventricle pressure (RVP), PAP and PCWP were recorded utilizing the Swan Ganz catheter proximal and distal lumens (Model 13 IHVF7, Edwards Lifesciences). Two pressure transducers (LOGICAL MX960, Medex) were connected to the Swan Ganz catheter lumens for simultaneous recording from two compartments. Noninvasive measurement of the respiratory flow was acquired simultaneously with the PCWP, utilizing a breathing mask with mounted flow sensor (ZAN 600, nSpire Health, Longmont, Colo., USA) connected to a differential pressure sensor (TSD160A, by Biopac systems Inc., Goleta, Calif., USA). The two pressures and the respiratory flow were connected to a data acquisition system (VIP 36, Biopac systems Inc., Goleta, Calif., USA) and to a portable PC with designated software for continuous acquisition and saving.

All patients were classified into three groups, according to the etiology: heart disease (HD), lung disease and mixed lung and heart diseases. Patients with clinical history and symptoms or signs of left heart failure (LHF), without or with insignificant lung disease were classified into the HD group. The lung group consists of patients with clinical history of lung disease without any history of left heart disease. The mixed group includes patients with a combined significant lung disease and signs or symptoms of left heart dysfunction. The lung group included patients with normal left ventricle (LV) EF, normal LV function and without coronary diseases. The lung group included patients with right ventricle dysfunction (without LV dysfunction) that might be secondary to the pulmonary hypertension.

The HD group patients were further labeled based on the HF etiology: ischemic (IHD), rheumatic (RHD), non-ischemic dilated cardiomyopathy (DCM), diastolic dysfunction without ischemia (DHD), and volume overload (VO). The Lung group was divided into main 3 subgroups: primary pulmonary hypertension (PAH), Obstructive lung diseases (OL), and parenchymal restrictive-type diseases (RL) that were associated with a decrease in lung compliance as scleroderma and interstitial lung diseases.

Signal Processing and the Respiratory Effort

Figure 1:
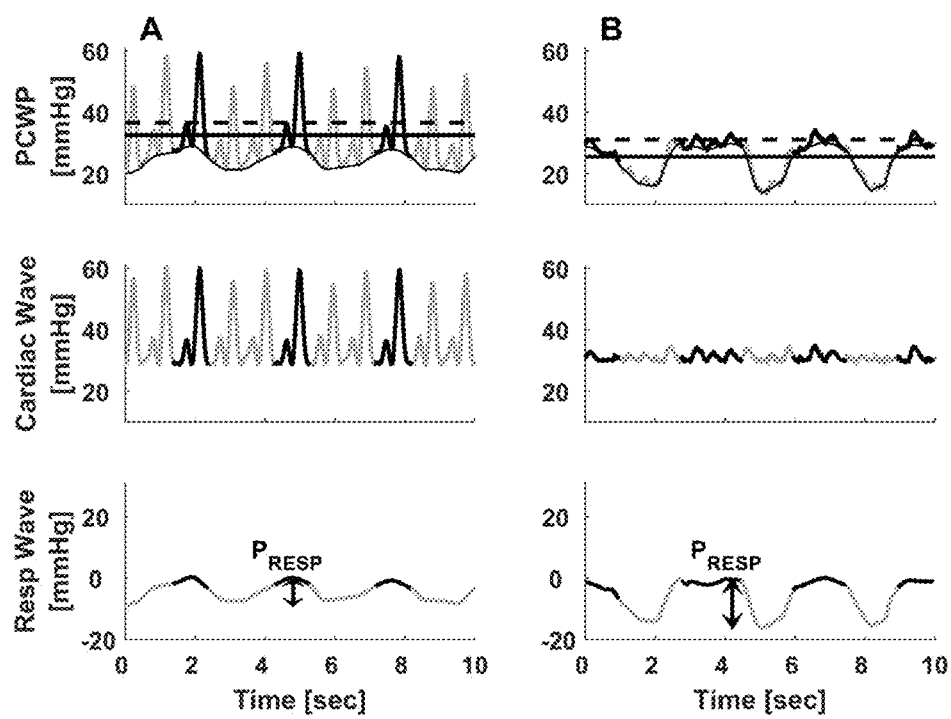
FIG. 1 is a graphical illustration of decomposition of the PCWP (upper) into cardiac (middle) and respiratory (lower) pressure waves, in two patients, one with prominent cardiac waves (A) and the other with prominent respiratory wave (B). The respiratory signal (lower panel) was derived by cubic interpolation through the local minima points in the original PCWP. The cardiac wave (middle) is identical to end-expiratory PCWP. The double-headed arrow depicts the respiratory effort (PRESP). The average PCWP (PCWPm) is marked with solid black thick line, while the end-expiratory PCWP (PCWPEE) is marked with dashed black line.

All intrathoracic pressures, including PAP and PCWP are affected by spontaneous breathing and decrease during the inspiratory phase. The PCWP was decomposed into two components representing the cardiac and respiratory waves. The respiratory wave was defined as the lower slow wave over which the cardiac waves were superimposed, as shown for two HF patients in FIG. 1, one with prominent cardiac waves (A) and one with prominent respiratory waves and diminished cardiac waves (B). The slow respiratory wave was detected by identifying the local minima points of the 'a' and 'v' cardiac waves in the PCWP. The respiratory wave was constructed using cubic interpolation through these points, as depicted in FIG. 1. Assuming that the pleural pressure is close to zero at end expiration, the respiratory wave zero level was set such that 95% of the wave falls below 0, and represents the pressure decrease during spontaneous inspiration. The remaining 5% represent the zero level and small upward deviations caused by noise and normal small variations in the end-expiratory volume. Subsequently, the cardiac wave (middle panel of FIG. 1) was calculated as the difference between PCWP and the respiratory wave. Note that the cardiac wave, the PCWP without the respiratory wave, is precisely the end expiratory PCWP (PCWPEE).

The respiratory effort, denoted as PRESP, is the peak-to-peak average value of the respiratory pressure wave (bottom of FIG. 1). The PCWPEE was calculated as the average value of PCWP at end expiration, and it is identical to the mean of the derived cardiac wave (FIG. 1). The mean PCWP (PCWPm) was calculated from the original PCWP, throughout the breath cycle, and is therefore lower than PCWPEE, as shown in FIG. 1. The end-expiratory PAP (PAPEE) and the mean PAP (PAPm) were measured in the same manner Data and Statistical Analyses The average values of PCWPm and PCWPEE were calculated over periods of 101.9±34.9 sec. PVR was calculated as the difference between PAPm and PCWPm, divided by the cardiac output (CO), while CO was determined by the thermodilution and the indirect Fick methods. The tidal volume (VT) was calculated by averaging the peak-to-peak changes in the integral of the respiratory flow.

Data analysis and statistics were performed using a designated software (Matlab, Mathworks). All average values are presented with the corresponding standard deviation, and the population estimates are presented with their standard error. 95% confidence interval is presented in square brackets, where applicable. The average values are compared using two-tailed uncoupled t-test, and proportions using z-test. All linear regression slope values were tested for significance (slope 0) using two-tailed t-test, with significance level of 0.05. Linear regression with non-significant slope was recalculated to find intercept with the slope value set to zero.

Results

The study enrolled 55 patients. Six patients were excluded from the analysis, four patients due to technical problems (no measurements of the PCWP or PAP) and two patients with normal hemodynamic indices but without clear clinical history relating to their lung functions. The remaining 49 patients were classified into one of the three groups: Heart Disease (HD) (N=29), lung diseases (N=14) and mixed lung and heart diseases (N=6). The HD and lung groups were similar in age and BMI. The NYHA class of the HD group was 3.1±0.8. The HD group (n=29) was heterogeneous and included patients with ischemic heart disease (IHD n=11), rheumatic heart diseases (RHD, n=7), non-ischemic diastolic dysfunction (DHD, n=6), non-ischemic dilated cardiomyopathy (DCM, n=3), and two cases of volume overload (VO) with cardiac index above 3.3 and signs and symptoms of heart failure (one due to multiple myeloma and the other with severe allergic inflammation and eruption). The HD group was divided into two subgroups, with preserved ejection-fraction (HFpEF) versus reduced EF (HFrEF). The majority of patients (n=19, 65.5%) had preserved ejection-fraction (EF≥50%) with a mean of 62.3±6.6%. The minority of the patients (n=10, 34.5%) had reduced EF of 19.5±11.1%. Most (70%) of the patients with HFrEF had ischemic heart disease and the rest non-ischemic cardiomyopathy. The Mixed group (n=6) included 4 patients with severe obstructive lung diseases (as patient with frequent COPD exacerbations, FEVI of 27% and DCM or patient with severe COPD with desaturations of Sa02=79% and rheumatic heart disease) and two patients with pulmonary hypertension that responded to sildenafil and iloprost, with preserved EF but LV diastolic dysfunction. The lung group (n=14) was also heterogeneous and included patients with primary pulmonary hypertension (n=3), severe COPD (n=1), scleroderma (n=6), lung cancer (n=2), and other restrictive lung diseases (n=2). The comorbidities of the HD and lung groups were different in the rate of chronic kidney disease and atrial fibrillation that were significantly higher in the HD group. In the laboratory tests the HD group had significantly higher creatinine level than the lung group.

The breathing had overt effects on the measured pressures in the different compartments.

Figure 2:
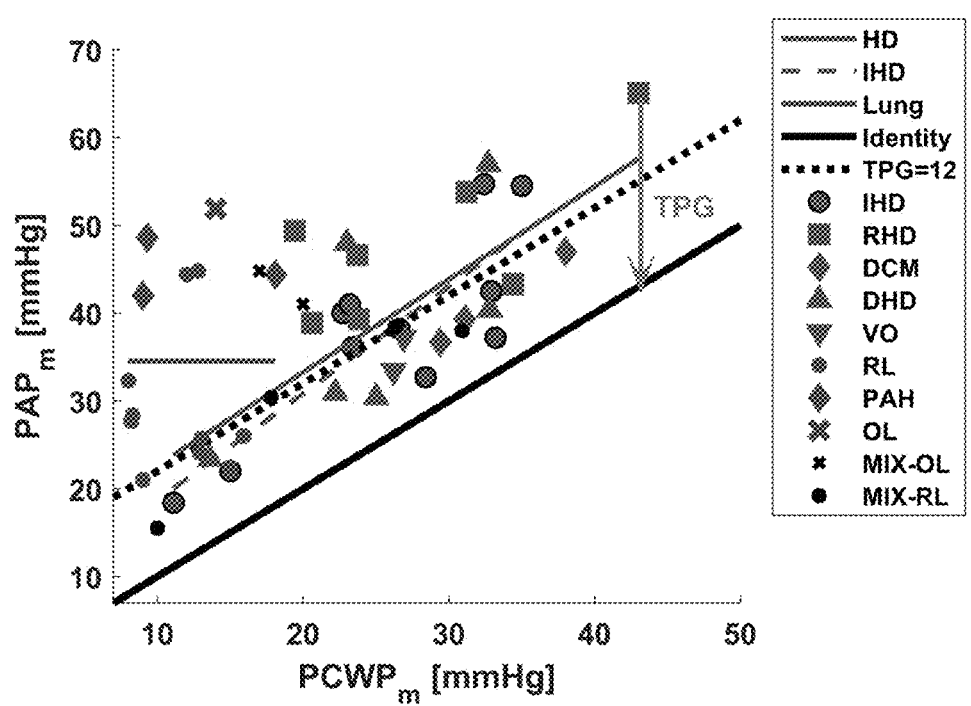
FIG. 2 is a graphical illustration of the relationships between the mean PAP and PCWP for the patients in the HD (red), Lung (blue) and Mixed (black) groups. A tight correlation existed between the PAP and PWCP for all the HD patients (n=29, red solid line) as well as for the subgroup of ischemic patients (n=11, red dotted line). There was no correlation between the two in the Lung group (blue line). The HD group included the following etiologies: ischemic (IHD, n=11, circles), rheumatic (RHD, n=7, squares), non-ischemic diastolic dysfunction (DHD, n=6, triangles) DCM (n=3, diamonds), and volume-overload (VO, n=2, inversed triangles). The lung group included subgroups of primary pulmonary hypertension (PAH, n=3, diamonds), restrictive lung disease (n=10, circles) and COPD (n=1, cross). The mixed group included patients that responded to arterial vasodilatation (MIX-RL, n=2, circle) and obstructive lung diseases (MIX-OL, n=4, cross). Thick black line is the identity line. The dotted black line depicts a trans-pulmonary pressure gradient (PAP-PCWP) of 12 mmHg. The arrow presents the trans-pulmonary pressure for a particular subject.

FIG. 2 depicts the relationships between the average PAP and PCWP, for both the HD (red-bordered symbols) and lung (blue bordered symbols) groups. There was a tight correlation (solid red line) between PAP and the PCWP in the HD group, for both the mean and end-expiratory values. These relationships relate to the entire heterogeneous group of the HD patients that includes patients with ischemic HD (IHD, circles), rheumatic heart diseases (RHD, squares), DCM (diamonds), non-ischemic diastolic dysfunction (DHD, triangle) and volume overload (VO, inversed triangles). Interestingly, identical slopes of the PAP-PCWP relationships were obtained for patients with HFpEF and patients with HFrEF. The ischemic subgroup of the HD patients had, slightly steeper but not statistically different slope. Fourteen patients in the HD group had trans-pulmonary pressure (TPG=PAP-PCWP) above 12 mmHg (data points above the black dotted line in FIG. 2). Four patients had "out of proportion" elevation of the PAP, defined as PVR over 3 Wood units combined with diastolic pressure gradient (DPG) above 7 mmHg. The lung group (blue symbols) had elevated average PAP (37.5±11.3 and 34.6±10.9 mmHg, respectively), that were independent of the PCWP (p=0.499, p=0.693, respectively). The heterogeneous lung group included patients with primary pulmonary hypertension (diamond), restrictive type of lung disease (circle) and COPD (cross). The mixed group patients (black symbols, n=6) that responded to sildenafil or iloprost (circle, n=2) or had obstructive lung diseases (cross, n=4) and heart diseases, represents a separate small mixed group. The symbols of the different groups are consistent throughout all the figures.

Figure 3:
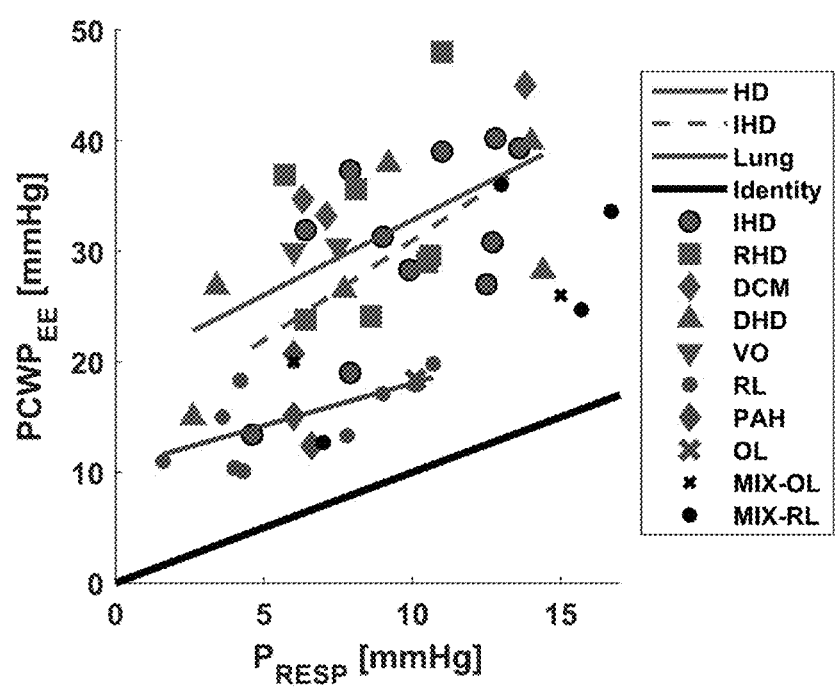
FIG. 3 is a graphical illustration of the relationships between the end-expiratory PCWP and the respiratory effort (PRESP). An increase in PRESP was associated with an increase in the PWCP in the HD group. The identity line (black) reveals that for all the patients PCWPEE was larger than PRESP: PCWPEE>PRESP. The symbols and lines are as defined in FIG. 2.

FIG. 3 presents the relationships between the end-expiratory PCWP and the respiratory effort (PRESP). The first striking observation is that patients with HD exhibited large respiratory efforts. The PRESP of the HD group spanned from 2.6 mmHg up to a huge effort of 14.4 mmHg with an average value of 9.0±3.2 mmHg Since the normal respiratory effort is about 2-3 mmHg the mean respiratory effort of the HD group was about 3.5 times the normal respiratory pressure and in some patients up to about 6 fold the normal effort.

There was a tight correlation between the PCWPEE and the respiratory effort, for all the patients. In the HD group, an increase of 1 mmHg in PRESP was associated with 1.35±0.40 [0.53 2.17] increase in the PCWPEE. The subgroup of the ischemic patients had a steeper slope of 1.80±0.76 [0.10 3.49]. Interestingly, a significant correlation was obtained between the PCWPEE and PRESP also for the lung group, with the slope of 0.77±0.29 [0.14 1.39].

The relationship between the PCWP and PRESP is commonly attributed to the increase in lung stiffness with the increase in the PCWP.

The increase in PCWP and PAP with PRESP cannot be attributed to changes in the cardiac output, as the mean cardiac output was 4.19±1.17 L/min in the HD group (4.04±1.36 L/min in the ischemic HD subgroup) and 4.53±1.49 L/min in the lung group, and the cardiac output was independent of PRESP in all the groups.

Figure 4:
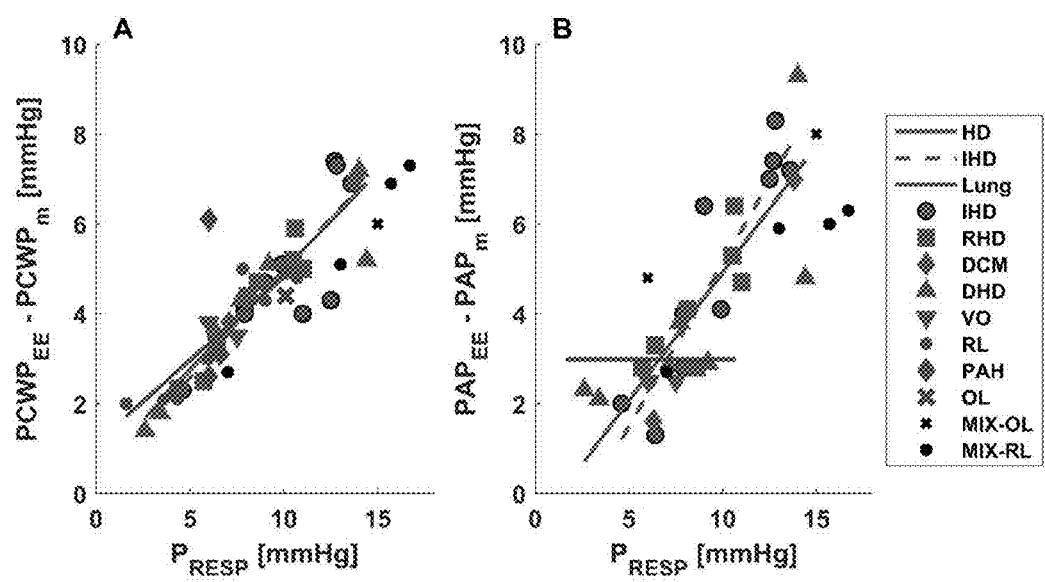
FIG. 4 is a graphical illustration of the differences between the end expiratory and the average PCWP (A) and PAP (B) increased with the respiratory effort. The symbols and lines are as defined in FIG. 2.

FIG. 4 presents the difference between the end-expiratory and the average values of the PCWP (A) and PAP (B) relative to the respiratory effort. The differences between these measurements were not negligible and were tightly dependent on the respiratory effort for patients with heart disease. As for the lung group, only the difference between PCWPEE and PCWPm was dependent on the respiratory effort, and it was identical to the dependence obtained in the HD group. A respiratory effort of 10 mmHg yielded a difference of 4.4±0.4 [3.6 5.3] mmHg and 3.7±0.9 [1.7 5.7] mmHg between PCWPEE and PCWPM in the HD and lung groups, respectively, with no statistical difference (p=0.315). A similar increase of 5.7±0.7 [4.3 7.1] mmHg in the difference between the PAPEE and PAPM was obtained for 10 mmHg increase in the respiratory effort, in the HD patients. In HD patients with the large respiratory effort, these differences in the PCWP and PAP were as high as 7.4 mmHg Similar results were obtained for the ischemic subgroup and for the preserved or reduced EF subgroups.

Discussion

The study suggests that the measured respiratory effort is a sign of cardiac decompensation. This stipulation is based on the following observations:

(1). HF patients exhibit high respiratory effort at rest, and the amplitude of their apparent respiratory effort (PRESP) reaches 14.4 mmHg, about 6 fold the normal PRESP (about 2-3 mmHg).

(3). An increase in PRESP is associated with a parallel proportional increase in PCWPEE, with a slope of 1.35±0.40 between the two, in the HD group.

(4) The differences between the end-expiratory and the average PCWP and PAP, increase with PRESP by 0.44±0.04 mmHg and 0.57±0.07 mmHg, respectively, reaching a difference of about 8 mmHg at the high PRESP. A large PRESP can yield PCWPEE above 15 mmHg and PAPEE above 25 mmHg while the mean PCWP and PAP are within the normal range. Thus, the respiratory effort may influence the diagnosis of elevated PCWP and pulmonary hypertension.

Respiratory Effort

Continuous monitoring of the intrathoracic impedance and the pulmonary artery pressure have established the gradual development of cardiac decompensation and the ability to detect it days before the patient becomes symptomatic and seeks medical assistance. The gradual nature of the decompensation raises the question what are the underlying mechanisms that drive the progressive deterioration. The present study revealed that the respiratory effort is also markedly elevated in HF patients and there is tight correlation between the severity of the respiratory effort and the other hemodynamic indices.

The patients in the HD group had a mean NYHA class of 3.1±0.8 (n=29) and they exhibited very high respiratory effort, on average 9.0±3.2 mmHg, about 3.5 fold the normal effort (around 2-3 mmHg). This high respiratory effort was observed while the patients were lying at rest during the catheterization, and were on optimal medical treatment.

The respiratory effort of the HF group in our cohort is substantially elevated not only relative to the normal baseline but also relative to the normal maximal effort. However, the maximal effort can be sustained only for a short time period of few breath cycles, while the HF patients have to maintain nonstop elevated respiratory effort to preserve the adequate blood oxygenation. Moreover, HF patients suffer from skeletal and respiratory muscles atrophy and decrease in the maximal respiratory muscle effort. Thus the observed increase in the respiratory effort is ominous in light of the expected decrease in their respiratory capabilities.

The Parallel Increase in the PCWP and the Respiratory Effort

A novel observation of the inventors' study is the tight correlation between PCWP and the respiratory effort. In contrast with the prior art, this is the first time that the respiratory effort is derived from the respiratory fluctuations of the hemodynamic measurements, and it is the first time that the PCWPEE is directly tied with the respiratory effort in patients with heart failure.

The data from all patients reveal that PCWPEE was always larger than the PRESP (all the data points in FIG. 2 were above the black identity line).

End-Expiratory Vs. Average Pressure Measurements

The end-expiratory measurements of the PCWP and PAP are consistently higher than the mean PCWP and PAP The difference between the end-expiratory and the average PCWP and PAP values increases with the increase in the respiratory effort (FIG. 4) and can reach 7.4 mmHg in patients with high respiratory effort.

The respiratory effort is defined hereinabove as the peak-to-peak change in the respiratory wave that was extracted from the PCWP signal. Measurement of the esophageal pressure was not included since it increases the risk and significantly complicates the RHC procedure. However, the invention also contemplates taking esophageal pressure into account.

Assessment of the respiratory effort from the PCWP can provide important information, which is currently ignored in the prior art. The definition of the respiratory effort as the peak-to-peak amplitude of the respiratory swing (FIG. 1) includes the sum of the inspiratory and the expiratory efforts. The invention also contemplates differentiating between the effects of the excessive inspiratory and expiratory efforts.

The range of the tested parameters PCWP, PAP, PVR and the respiratory effort spanned over wide ranges, including close to the normal values, in accordance with the invention, support the validity of the suggested interactions between the respiratory and pulmonary circulatory systems.

What is claimed is:

1. A method for detecting or monitoring respiratory or cardiac health of a patient, comprising:
   measuring any intravascular or intracardiac pressure (IVP) within a chest of a patient over a period of time, said IVP including a measured respiratory wave;
   defining respiratory effort of the patient as a peak-to-peak amplitude of said respiratory wave; and
   using said respiratory effort to detect or monitor respiratory and cardiac health of the patient by comparing said respiratory effort with a known value of respiratory effort or by monitoring changes in said respiratory effort of the patient over another period of time, wherein, if monitoring changes in said respiratory effort of the patient shows an increase in the respiratory effort, then said increase is used to alert of an increase in workloads of ventricles of the patient.

2. The method according to claim 1, wherein said IVP comprises pulmonary capillary wedge pressure (PWCP).

3. The method according to claim 1, wherein said IVP comprises pulmonary artery pressure (PAP).

4. The method according to claim 1, wherein said IVP comprises left atrial pressure.

5. The method according to claim 1, wherein said peak-to-peak amplitude is an average peak-to-peak amplitude over said period of time.

6. The method according to claim 1, wherein if monitoring changes in said respiratory effort of the patient shows an increase in the respiratory effort, then said increase is used to alert of an increase in pulmonary capillary wedge pressure (PWCP) of the patient.

7. The method according to claim 1, wherein if monitoring changes in said respiratory effort of the patient shows an increase in the respiratory effort, then said increase is used to alert of an increase in a pulmonary vascular resistance (PVR) of the patient.

8. The method according to claim 1, wherein if monitoring changes in said respiratory effort of the patient shows an increase in the respiratory effort, then said increase is used to alert of an increase in a pulmonary artery pressure (PAP) of the patient.

9. The method according to claim 1, wherein if monitoring changes in said respiratory effort of the patient shows an increase in the respiratory effort, then said increase is used to alert of an increase in a pulmonary congestion of the patient.

10. The method according to claim 1, comprising using said respiratory effort to detect dyspnea of the patient.

11. The method according to claim 1, comprising using said respiratory effort to monitor dyspnea of the patient.

12. The method according to claim 1, comprising using said respiratory effort to detect pulmonary hypertension of the patient.

13. The method according to claim 1, comprising using said respiratory effort to monitor pulmonary hypertension of the patient.

14. The method according to claim 1, wherein if said respiratory effort is higher than a known value of respiratory effort, then the patient is diagnosed as developing an event of cardiac decompensation.

15. The method according to claim 2, comprising using said respiratory effort to detect lung health, wherein if said PCWP and said respiratory effort both increase over time, then the patient is diagnosed as having a progression of heart failure.

16. The method according to claim 1, further comprising calculating an end expiratory IVP without asking the patient to withhold breathing at the end expiratory, by decomposition of the respiratory wave and a cardiac wave from the intravascular pressure measurement.

17. The method according to claim 1, further comprising presenting said respiratory effort, and mean intravascular pressure with said respiratory wave.

18. The method according to claim 1, further comprising presenting said respiratory effort, and mean intravascular pressure without said respiratory wave.

19. The method according to claim 1, further comprising presenting said respiratory effort, end-expiratory intravascular pressure, and mean intravascular pressure with said respiratory wave.

20. The method according to claim 1, further comprising presenting said respiratory effort, end-expiratory intravascular pressure, and mean intravascular pressure without said respiratory wave.

21. A tangible computer-readable device having instructions stored thereon that, when executed by at least one computing device, causes the at least one computing device to perform operations comprising:
measuring any intravascular or intracardiac pressure (IVP) within a chest of a patient over a period of time, said IVP including a measured respiratory wave;
defining respiratory effort of the patient as a peak-to-peak amplitude of said respiratory wave; and
using said respiratory effort to detect or monitor respiratory and cardiac health of the patient by comparing said respiratory effort with a known value of respiratory effort or by monitoring changes in said respiratory effort of the patient over another period of time, wherein, if monitoring changes in said respiratory effort of the patient shows an increase in the respiratory effort, then said increase is used to alert of an increase in workloads of ventricles of the patient.

22. The device according to claim 21, wherein said IVP comprises pulmonary capillary wedge pressure (PWCP).

23. The device according to claim 21, wherein said IVP comprises pulmonary artery pressure (PAP).

24. The method according to claim 21, wherein said IVP comprises left atrial pressure.

* * * * *